(12) United States Patent
Borg et al.

(10) Patent No.: US 8,671,958 B2
(45) Date of Patent: Mar. 18, 2014

(54) ORTHODONTIC FLOSSER

(76) Inventors: N. Michelle Borg, Paradise, CA (US);
John O. H. Niswonger, Calabasas, CA (US)

( * ) Notice: Subject to any disclaimer, the term of this patent is extended or adjusted under 35 U.S.C. 154(b) by 15 days.

(21) Appl. No.: 13/196,302

(22) Filed: Aug. 2, 2011

(65) Prior Publication Data
US 2011/0284023 A1  Nov. 24, 2011

Related U.S. Application Data

(63) Continuation-in-part of application No. 12/904,058, filed on Oct. 13, 2010, now Pat. No. 8,387,629.

(60) Provisional application No. 61/251,609, filed on Oct. 14, 2009.

(51) Int. Cl.
*A61C 15/00* (2006.01)

(52) U.S. Cl.
USPC ........................................................ 132/325

(58) Field of Classification Search
USPC .................. 132/323, 324, 325, 326, 327–329
See application file for complete search history.

(56) References Cited

U.S. PATENT DOCUMENTS

| | | | |
|---|---|---|---|
| 205,252 A | 8/1936 | Sonnenberg | |
| 2,052,520 A * | 8/1936 | Sonnenberg | 132/324 |
| 3,734,107 A * | 5/1973 | Thierman | 132/325 |
| 3,746,017 A * | 7/1973 | Casselman | 132/325 |
| 3,924,647 A * | 12/1975 | Lindblad | 132/326 |
| 4,901,742 A * | 2/1990 | Olson | 132/325 |
| 5,184,631 A | 2/1993 | Ikeda | |
| 5,482,466 A * | 1/1996 | Haynes | 132/323 |
| 5,495,683 A | 3/1996 | Miotto et al. | |
| 5,603,921 A * | 2/1997 | Bowen | 424/49 |
| 5,678,578 A | 10/1997 | Kossak | |
| 5,782,250 A * | 7/1998 | Harrah, Jr. | 132/327 |
| 5,860,434 A * | 1/1999 | Sines et al. | 132/323 |
| 5,947,133 A | 9/1999 | Kossak | |
| 6,488,036 B1 | 12/2002 | Francis | |
| 6,874,509 B2 | 4/2005 | Bergman | |
| 7,011,099 B2 | 3/2006 | Bergman | |
| 7,467,631 B2 | 12/2008 | Bergman et al. | |
| 2006/0011212 A1 | 1/2006 | Achepohl | |
| 2007/0017546 A1 * | 1/2007 | Brown | 132/323 |
| 2007/0204879 A1 * | 9/2007 | Chen et al. | 132/325 |
| 2009/0241984 A1 * | 10/2009 | Wall | 132/323 |

* cited by examiner

*Primary Examiner* — Robyn Doan
*Assistant Examiner* — Brianne Kalach
(74) *Attorney, Agent, or Firm* — Ronald L. Rohde

(57) ABSTRACT

An orthodontic flosser comprising an elongated handle and a head coupled to the handle at a vertical angle is disclosed. A first and second projection extend from the head for suspending floss, the first projection is sized for insertion of floss between a wire affixed to a tooth and the tooth. A source spool of fresh floss is configured to feed fresh floss incrementally into suspension between the first and second projections while a take-up bobbin is configured for taking up used floss and applying tension to the suspended floss. A button may be used for releasing the source spool to rotate, and for holding the source spool against rotation. The source spool and take-up bobbin may be disposed in separated chambers to reduce cross contamination.

20 Claims, 11 Drawing Sheets

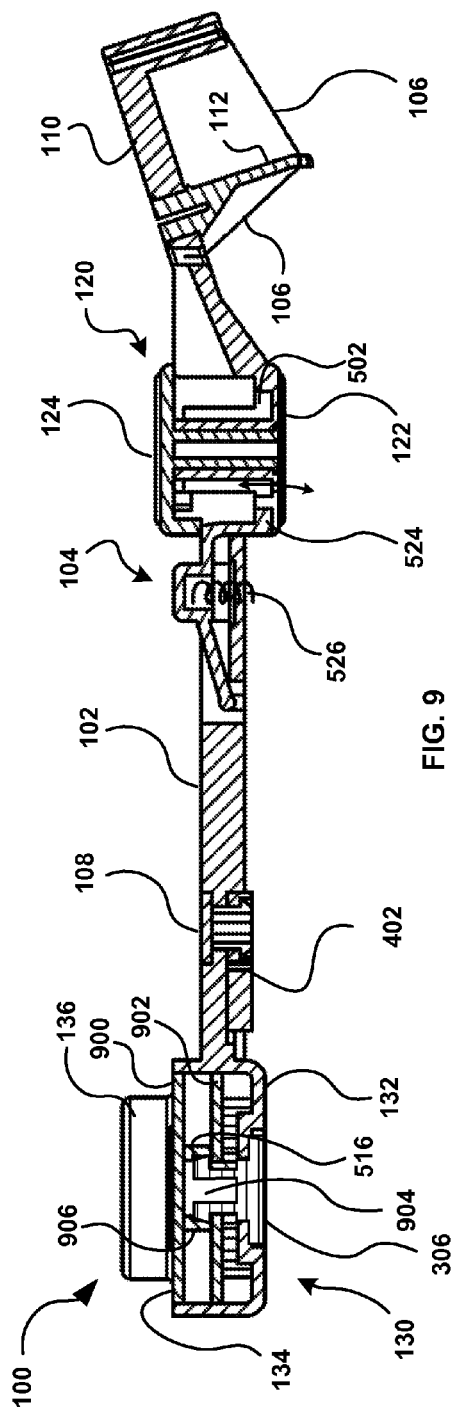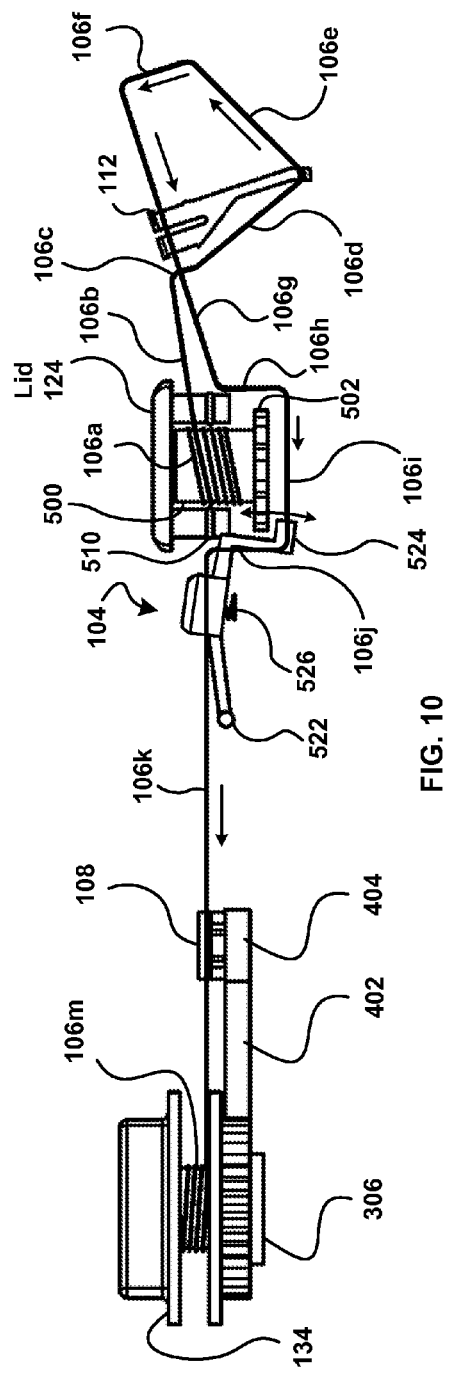

ORTHODONTIC FLOSSER

CROSS-REFERENCE TO RELATED APPLICATIONS

The present application is a continuation in part of U.S. patent application Ser. No. 12/904,058, filed on Oct. 13, 2010 now U.S. Pat. No. 8,387,629 which in turn claims priority and benefit to U.S. provisional patent application Ser. No. 61/251,609 filed on Oct. 14, 2009 titled "ORTHODONTIC FLOSSER," and is related to U.S. provisional patent application Ser. No. 61/241,281, filed on Sep. 10, 2009 and titled "ANTI-MICROBIAL ORTHODONTIC FLOSS." All of the above applications are incorporated by reference herein in their entirety.

BACKGROUND

1. Field of the application

The present application relates generally to a flossing apparatus, and more particularly to an orthodontic flosser.

2. Description of Related Art

Flossing is particularly important for people who have braces. Braces typically include brackets bonded to the surfaces of two or more teeth and a wire or archwire affixed to the brackets. Flossing around braces may be accomplished by threading the floss between the braces and the teeth and then maneuvering a length of the floss into contacts between adjacent teeth. Upon flossing around a pair of teeth and braces, the floss is generally pulled out and then threaded into another position for the next pair of teeth. Unfortunately, threading, inserting, manipulating the floss around the braces, and removing the floss for each pair of teeth can be difficult and time consuming. Maintaining tension on the floss while manipulating the floss between teeth and around braces involves a degree of dexterity and skill that is often beyond the ability of many children and even adults. Frustration due to the difficulty of acquiring skills, manipulating the floss, and the extra time involved in threading and removing the floss can discourage flossing. The purpose of flossing is to remove debris and contamination from contacts between teeth and surfaces around braces to prevent interproximal tooth decay and gum disease. Debris includes particulate matter, dental plaque, and bio films. Contamination includes bacteria. Dental plaque tends to adhere to surfaces such as teeth and wires. Floss generally picks up debris and contamination from surfaces of the teeth and the braces in the removal process. Unfortunately, the floss can then redistribute the debris and bacteria to other teeth interproximal spaces and braces around the mouth, thus, causing further spreading of tooth decay and gum disease.

SUMMARY

A flosser for cleaning contacts between two teeth attached to a wire brace includes a handle coupled to a head at an upward angle with respect to the handle. A pair of projections are configured for feeding fresh floss into suspension and supporting the fresh floss under tension. A source spool for dispensing fresh floss may be coupled to the handle, and a take-up bobbin for accumulating used floss and advancing the floss through the flosser may also be coupled to the handle. The source spool and the take-up bobbin cooperate to apply tension to the floss. A button may be configured to release the source spool to rotate when pressed for dispensing the floss. The button is also configured to prevent rotation of the source spool for applying tension to the floss when not pressed. A source chamber for enclosing the source spool may reduce exposure of fresh floss to dirty debris and contamination such as bacteria. A take-up chamber for enclosing used floss on the take-up bobbin may contain contamination and debris on the used floss and further reduce exposure of the fresh floss to contamination and debris. The source chamber and the take-up chamber may be separated by a portion or all of the handle to reduce cross contamination. Grooves and/or channels may be disposed along the handle, the head, and the source chamber to permit handling of the flosser without touching the floss or interfering with motion of the floss through the flosser, thus, further reducing cross-contamination.

Various embodiments of the technology include a flosser having a floss support having an aperture configured for slidably supporting floss and sized for insertion of the aperture between a wire mounted on a pair of adjacent teeth and an interproximal space between the teeth and a floss guide about parallel to the floss support and configured for slidably supporting floss in suspension between the aperture and the floss guide The flosser further includes a head for supporting the floss support and the floss guide and a a source spool configured for rotatably dispensing floss to the floss support. The floss support may be longer than the floss guide. A button assembly may be configured to release the source spool for rotation when a button of the button assembly is pressed and to prevent rotation of the source spool when the button is not pressed. A source chamber may be configured to enclose the spool to prevent contamination of floss on the source spool. The flosser further includes a receiving spool configured for rotatably receiving floss after use, the receiving spool including a ratchet configured for unidirectional rotation of the receiving spool and to hold tension on the floss when the button is not pressed. A pawl may be configured to engage a face of a ratchet tooth about normal to the engaged face. A receiving chamber separated from the source chamber may be configured to enclose the receiving spool to contain contamination on the received floss. The flosser also includes a handle coupled to the head and configured to support the source chamber and the receiving chamber, the handle forming an angle with respect the head, a plane defined by the angle between the head and the handle about parallel to the floss support and the floss guide.

Various embodiments of the technology include an apparatus for cleaning teeth, the apparatus having an elongated handle configured for dispensing fresh floss, a head coupled to the handle at an upward angle and a pair of projections depending in the plane of the upward angle downward from the head and configured to slidably suspend fresh floss under tension. The apparatus further includes a first spool supported on the elongated handle and configured to provide fresh floss to the pair of projections and to maintain resistance to tension on the fresh floss during use of the fresh floss for cleaning teeth and a second spool supported on the elongated handle and configured to apply tension to the fresh floss when resistance to tension is maintained at the first spool and to receive used floss from the pair of projections when resistance to tension is released at the first spool. The apparatus also has a button assembly configured to release resistance to tension at the first spool.

Various embodiments of the technology include a flosser for cleaning a contact between two teeth attached to a wire brace. The flosser includes a handle and a head coupled to the handle, the head and the handle forming an upward angle. The handle may be coupled to a source spool for dispensing floss to the head and a button configured to release the source spool to rotate when pressed for dispensing the floss, the button may further configured to prevent rotation of the source spool when not pressed for applying tension to the floss. A first floss support may be coupled to the head and extend downward from the head in a plane formed by the angle between the head and the handle. A second floss support may extend from the head about parallel to the first floss support and include an aperture sized for feeding the floss from the source spool into suspension between the first and second floss support. The second floss support is shaped for insertion of the aperture into a space between the wire brace and the two teeth for cleaning the contact between the two teeth using suspended floss. The flosser further includes a take-up bobbin coupled to the handle for receiving floss from the first floss support after use and for pulling unused floss through the aperture, the take-up bobbin and the source spool configured to apply tension to the suspended floss and to hold the tension when the button is not pressed. The second floss support may be longer than the first floss support.

BRIEF DESCRIPTION OF THE DRAWINGS

FIG. 9 is a side cross section of the flosser of FIG. 1 along line b-b of FIG. 3.
FIG. 10 is a side elevation of internal parts of the flosser of FIG. 1.

DETAILED DESCRIPTION

Figure 1:
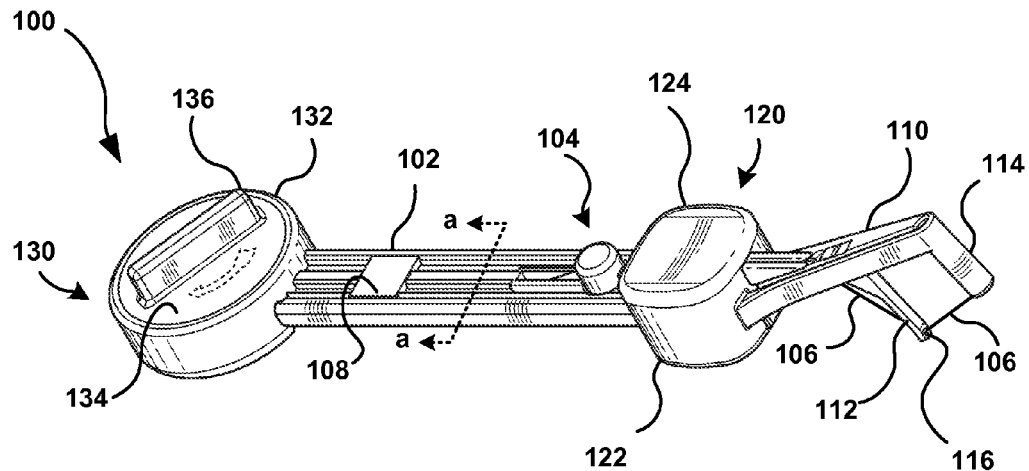
FIG. 1 is a top perspective view of an embodiment of a flosser, in accordance with aspects of the technology.
Figure 2:
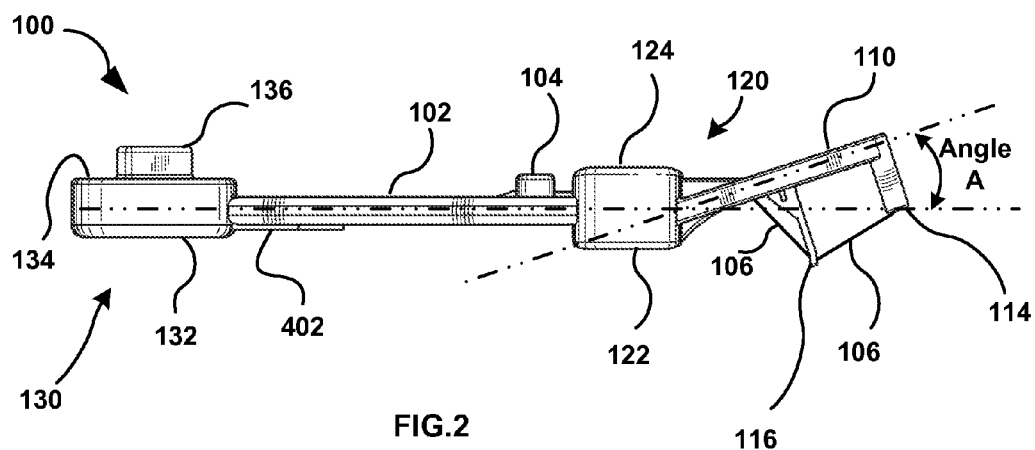
FIG. 2 is a right side elevation of the flosser of FIG. 1.

FIG. 1 is a top perspective view of an embodiment of a flosser 100, in accordance with aspects of the technology. FIG. 2 is a side elevation of the flosser 100 of FIG. 1. The flosser 100 includes a handle 102, a head 110, a source assembly 120 for dispensing floss 106 to the head 110 before use (fresh floss), and a receiving assembly or take-up assembly 130 for collecting floss 106 from the head 110 after it has been used (used floss). The handle 102 is configured to support the source assembly 120, the take-up assembly 130, and the head 110. The head 110 of FIG. 1 extends from the source assembly 120 and includes a support or projection 112 and a support, feed guide, or guide 114. Floss 106 may be supported and suspended between projection 112 and the guide 114 (suspended floss). In various embodiments, the head 110 is coupled to the handle, the take-up assembly 130 and/or the source assembly 120. The guide 114 of FIG. 1 is in the shape of a tube. However, other shapes include a trough, a channel, aperture on a projection, etc. The source assembly 120 is illustrated as being disposed at an end of the handle 102 adjacent the head 110. However, the source assembly 120 may be disposed at various locations along the handle 102. Similarly, the take-up assembly 130 may be disposed at various locations along the handle 102. In some embodiments, the positions of the source assembly 120 and the take-up assembly 130 may be reversed with respect to those illustrated in FIG. 1.

The head 110 may be disposed at upward angle A from the handle 102, as illustrated in FIG. 2. A dotted line represents an axis of the handle 102 and another dotted represents an axis of the head 110 in FIG. 2. The dotted lines are for assisting in visualization of the angle A and are not part of the flosser 100. The upward angle A between the handle 102 and the head 110 may promote ergonomics and use of the flosser 100. For example, the angle may improve visibility of the floss 106 under the handle 102 during use. In various embodiments, the angle A is about 10, 11, 12, 13, 14, 15, 16, 17, 18, 19, 20, 23, 25 or more degrees. The projection 112 and the guide 114 may depend downwardly from the head in about the plane of the angle A between the head 110 and the handle 102. The projection 112 and the guide 114 may be about normal to the head 110 and about parallel to each other. The projection 112 of FIG. 2 is longer than the feed guide 114. This may also promote ergonomics and use of the flosser 100. For example, a shorter feed guide 114 may reduce interference with a tongue and/or the roof of the mouth of a user and increase range of motion of the projection 112. In various embodiments, the projection 112 is 2, 3, 4, 5, 6, 7, 8, 9, 10 or more millimeters longer than the feed guide 114.

A support aperture or projection aperture 116 may be disposed near a tip of the projection 112 and configured to support floss 106. Floss 106 may be suspended between the tube of the feed guide 114 and the support aperture 116. The support aperture 116 is configured to support the floss 106 near the tip of the projection 112. The support aperture 116 may be sized for floss 106 to slide through freely or with a desired resistance. The flosser 100 further includes a button assembly 104 disposed on the handle 102. The button assembly 104 engage and disengaged a spool in the source assembly 120 as described more fully elsewhere herein.

The source assembly 120 is configured to enclose and floss 106 from contamination and debris before use. The source assembly 120 is further configured to pay out floss 106 to the projection 112 while the button assembly 104 is disengaged. The source assembly 120 includes a source chamber 122, a lid 124, and a spool (illustrated elsewhere herein). The source chamber 122 and the lid 124 may enclose floss 600 and prevent contamination and debris from splashing and falling on enclosed floss 600. The take-up assembly 130 is configured to receive and accumulate the floss 106 after use. The take-up assembly 130 includes a take-up chamber 132, and take-up (or receiving) bobbin (or spool) 134. The bobbin 134 includes a bobbin grip 136 configured for use in rotating the bobbin 134 to wind the floss 106 around the bobbin 134 after use and draw the floss 106 through the flosser 100 while the button assembly 104 is actuated. Winding the floss 106 around a spindle of the bobbin 134 using the grip 136 may further serve to apply tension to the floss 106 while the button assembly 104 is engaged. The bobbin 134 and take-up chamber 132 are configured to enclose floss 106 to contain contamination and debris disposed on the floss 106 during use. The source chamber 122 and take-up chamber 132 may be physically separated structures disposed along the handle 102 to reduce cross contamination of debris and bacteria from the take-up chamber 132 to the source chamber 122. The source chamber 122 and take-up chamber 132 may disposed at opposite ends of the handle 102 or separated by a portion of the handle 102.

Figure 3:
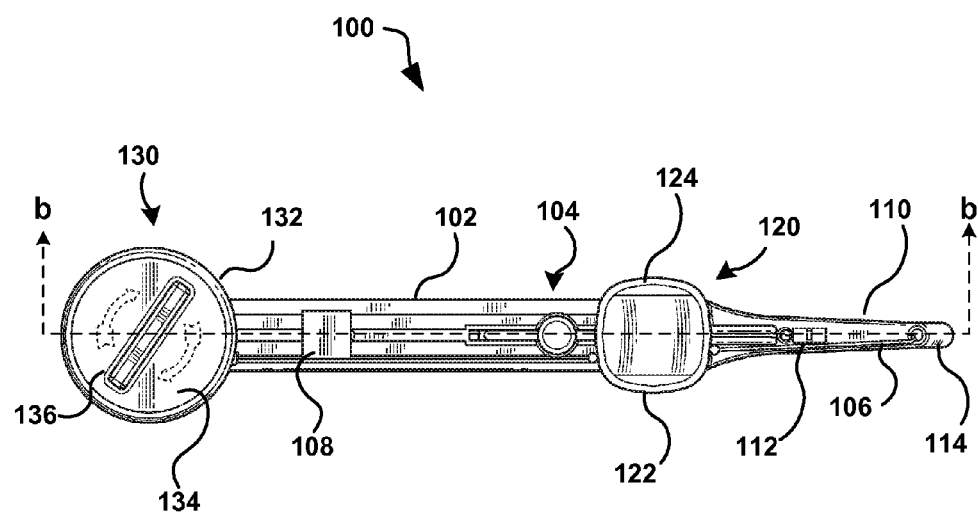
FIG. 3 is a top plan view of the flosser of FIG. 1.
Figure 4:
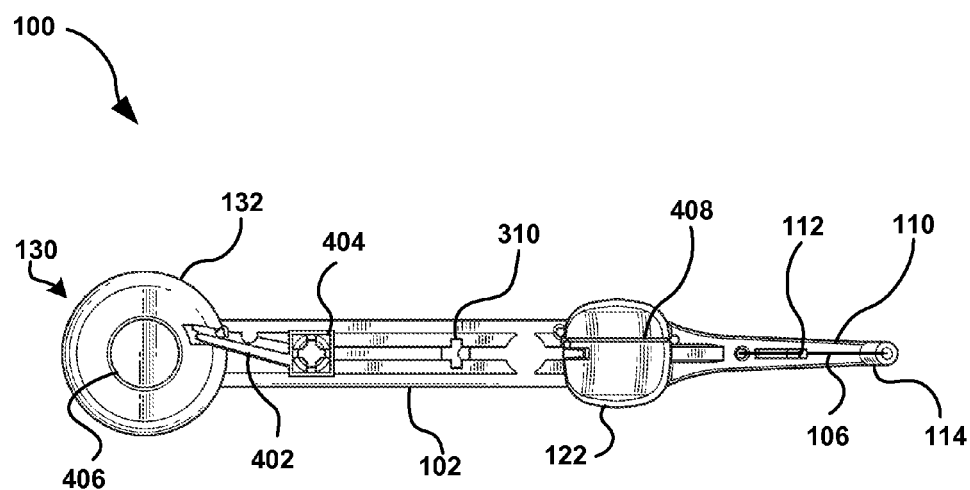
FIG. 4 is a bottom plan view of the flosser of FIG. 1.

FIG. 3 is a top plan view of the flosser 100 of FIG. 1. FIG. 4 is a bottom plan view of the flosser 100 of FIG. 1. FIG. 4 illustrates a pawl 402 and a pawl mount 404. The pawl 402 is configured to engage a sprocket disposed on the bobbin 134 to provide for one-way rotation of the bobbin 134. The pawl mount 404 illustrated in FIG. 4 (also FIGS. 1 and 3) may secure the pawl 402 to the handle 102. A bobbin lock 406 may secure the bobbin 134 within the take-up chamber 132. A button socket 310 may secure the button assembly 104 rotatably to the handle 102. A groove 408 may provide a path for slidable movement of floss 106 between the head 110 and the handle 102 after use.

Figure 5:
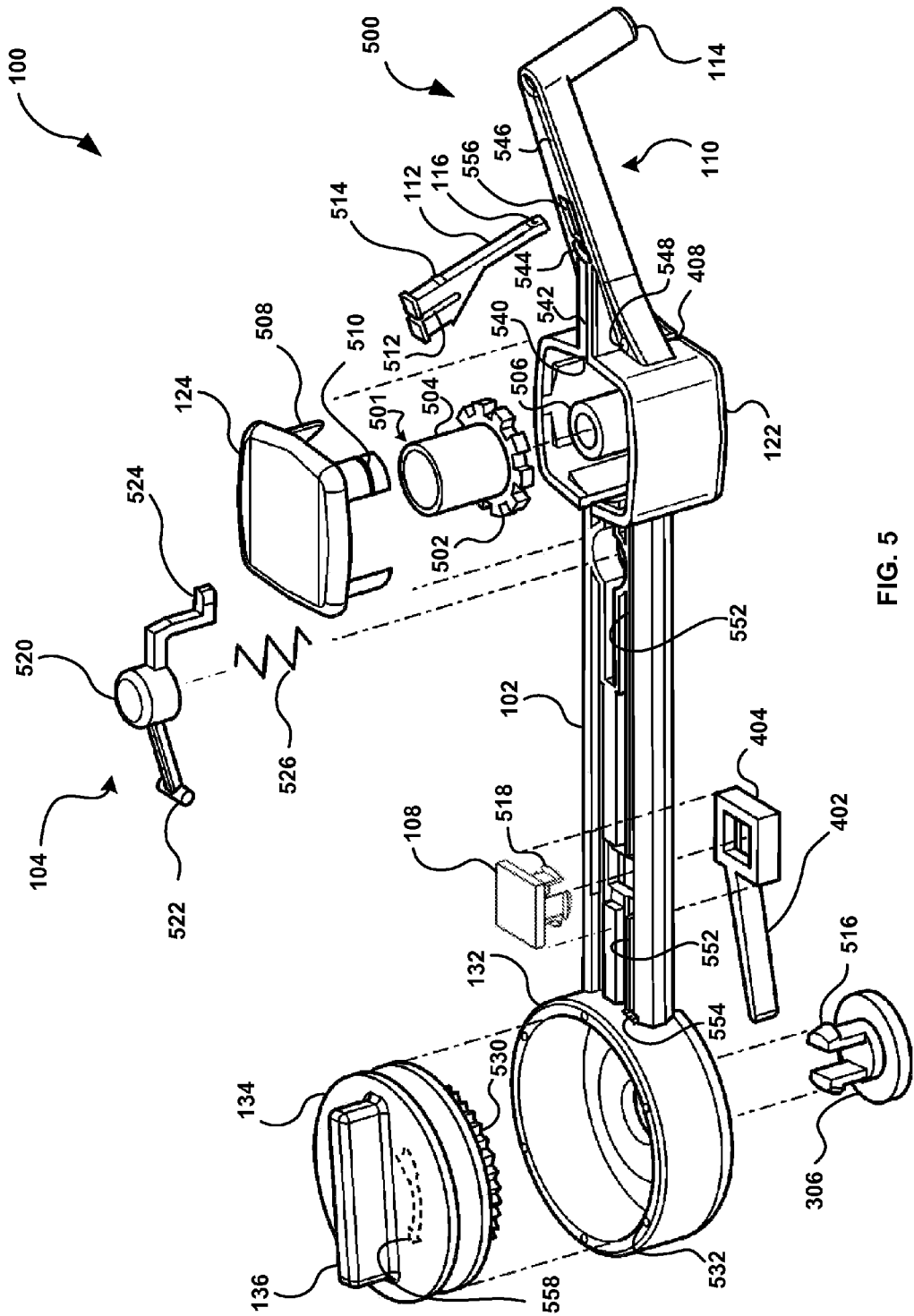
FIG. 5 is an exploded perspective view illustrating exemplary internal components the flosser of FIG. 1, in accordance with aspects of the technology.
Figure 6:
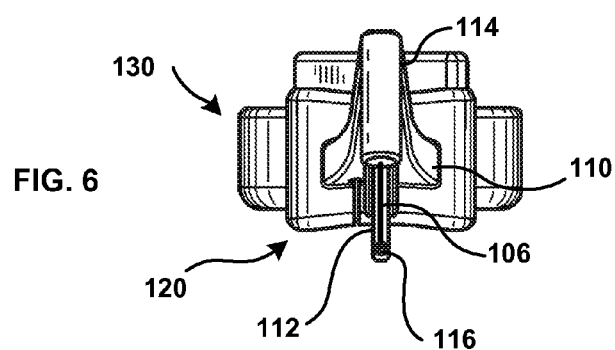
FIG. 6 is an enlarged front elevation of the flosser of FIG. 1.
Figure 7:
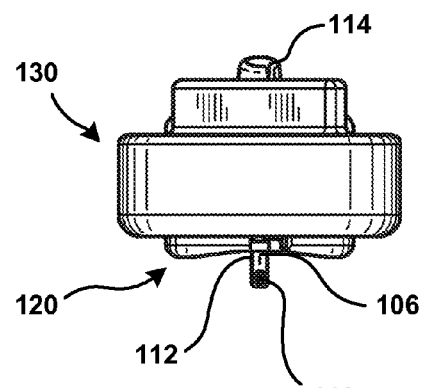
FIG. 7 is an enlarged rear elevation of the flosser of FIG. 1.

FIG. 5 is an exploded perspective view illustrating exemplary internal components the flosser 100 of FIG. 1, in accordance with aspects of the technology. FIG. 6 is an enlarged front elevation of the flosser 100 of FIG. 1. FIG. 7 is an enlarged rear elevation of the flosser 100 of FIG. 1. A body 500 comprises the handle 102, the source chamber 122, take-up chamber 132, and the head 110. The body 500 of FIG. 5 is illustrated as having been fabricated from a single piece of material, for example using injection molding processes. However, the body may be fabricated using multiple connected pieces.

The source assembly 120 of FIG. 5 further includes a source spool 501. The source spool 501 includes a spindle 504 upon which floss 106 may be wound for dispensing and use. In some embodiments, the floss is wound before assembly of the source spool 501 into the source chamber 122. In various embodiments, 1, 2, 3, 4, 5, 6, 7, 8, 10, 15, 20, or more meters of floss may be wound on the source spool 501. A cog 502 is configured to control unwinding of floss from the spindle 504 for the source spool. The cog 502 is further configured to rotate on a bearing 506. The lid 124 includes locator projections 508 configured to position the lid 124 and engage corners of the source chamber 122. An optional detent 510 disposed on the locator projections 508 may engage a groove within the corners (not illustrated) to secure the lid to the source chamber 122.

A slot 540 in the source chamber 122 is configured to feed floss 106 dispensed from the source spool 501 into a channel 542. The channel 542 is configured to provide a path for floss 106 from the first aperture 540 to a second aperture 544. The second aperture 544 is configured to provide a path for floss 106 between the upper surface of the head 110 and the projection aperture 116. The projection 112 of FIG. 1 is a separate component and is configured for insertion into an aperture 556 in the head 110. An optional slot 512 may provide additional flexibility during insertion. An optional detent 514 may secure the projection within the aperture 556. In various embodiments, the projections 112 is secured in the aperture 556 using an interference fit, adhesive, a fastener, a sonic weld, a heat weld, and/or the like. In some embodiments, the head 110 and the projection 112 are fabricated as a single piece.

Figure 8:
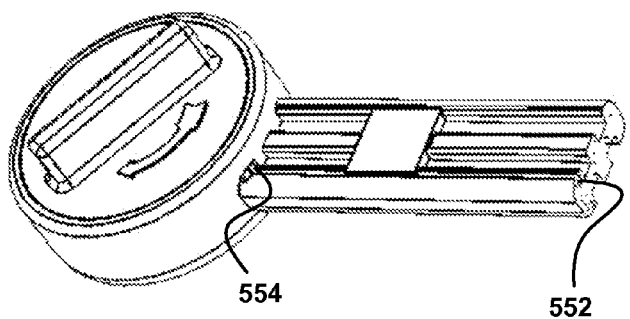
FIG. 8 is a perspective cross section of the handle of the flosser of FIG. 1 taken along line a-a.

A channel 546 may provide a path for floss 106 from the feed guide 114 to a third aperture 548. The third aperture 548 is configured to provide a path for floss 106 from the upper surface of the head 110 to the groove 408. The groove 408 is configured to provide a path for floss 106 from the third aperture 548 to the fourth aperture 550 (illustrated in FIG. 12). The fourth aperture 550 is configured to provide a path for floss 106 from the groove 408 to a handle channel 552. The handle channel 552 may be disposed as a longitudinal channel extending the length or a portion of the length of the handle 102. FIG. 8 is a perspective cross section of the handle of the flosser of FIG. 1 taken along line a-a, illustrating the handle channel 552. The handle channel 552 of FIG. 5 is configured to extend longitudinally along the handle 102 from the fourth aperture 550 to a fifth aperture 554, and provide a path for sliding floss 106. The handle channel 552 may permit the handle 102 to be gripped without touching or interfering with floss 106, thus, permitting free movement or sliding of the floss 106 along the handle 102 through the channel 552. The fourth aperture 554 provides a path through a side of the take-up chamber, from the handle channel 552 to the bobbin 134. Rotation of the bobbin 134 may draw floss 106 from the source spool 501 in a sliding motion through the various apertures (540, 544, 116, 548, 550, and 554), the various channels (542, 546, 552), the groove 408, and the feed guide 114 while the source spool pays out additional floss 106. Edges of the various apertures, channels, grooves, and guides may include a radius for reducing friction between floss 106 and the flosser 100.

The button assembly 104 of FIG. 5 includes a button 520, a pivot 522, an engagement pawl 524, and a spring 526. The pivot is configured to rotate within the button socket 310. The spring 526 may bias the button assembly 104 in the engagement position when the button 520 is not pressed. The engagement pawl 524 is configured to engage the cog 502 and prevent rotation of the source spool 501 when the button 520 is released and the button assembly 104 is in the engagement position. The engagement pawl 524 may hold the source spool 501 against tension on the floss 106. The button 520 may be pressed to move the button assembly to the disengagement position, thus, releasing the source spool 501 to rotate freely. Tension on the floss 106 may cause the source spool 501 to rotate and dispense floss 106. Rotation of the take-up bobbin 134 may cause the source spool 501 to rotate and dispense additional floss 106. Rotation of the take-up bobbin 134 may cause additional tension to be applied to the floss 106 when the engagement pawl 524 is in the engagement position. An illustration of the button assembly 104 in the engaged position is shown in FIG. 9, as discussed elsewhere herein. An illustration of the button assembly 104 in the disengaged position is shown in FIG. 10, as discussed elsewhere herein.

FIG. 9 is a side cross section of the flosser of FIG. 1 along line b-b of FIG. 3. The bobbin 134 includes an upper flange 900 supporting the grip 136, a lower flange 902 supporting a ratchet 530 and a spindle 906. An optional spindle aperture 904 is disposed in the spindle 906. In some embodiments, the bobbin 134, the upper flange 900, the lower flange 902, the spindle 906, the grip 136 and/or the ratchet 530 are fabricated from a single piece of material, for example, using an injection molding process. The ratchet 530 is configured to engage the pawl 402 for holding the bobbin 134 against rotation while the floss 106 is under tension for constraining the spool against turning in a first direction and permitting the bobbin 134 to turn in a second direction. As illustrated in FIG. 5, the pawl 402 permits clockwise rotation of the bobbin 134 (in the direction of arrows 558 disposed on the spool) while preventing counter-clockwise rotation of the bobbin 134, e.g., while the floss 106 is under tension.

A bobbin lock 306 may secure the bobbin 134 within the take-up chamber 132 using snap projections 516 engaging the lower flange 902. Moreover, the snap projections 516 may be inserted into the spindle aperture 904, rendering them inaccessible once engaging the lower flange 902, thus, preventing inadvertent removal of the bobbin 134 after assembly. Two snap projections 516 are illustrated in FIG. 5, however, 1, 3, 4, 5, 6, 7, 8, 9, 10, or more snap projections 518 may be used. The take-up chamber 132 optionally includes indicia 532 configured to indicate an angular position of the bobbin grip 136. In various embodiments, 2, 3, 4, 6, 8, 12, or more indicia 532 may be disposed about the upper surface of the take-up chamber 132. An image of an arrow may be disposed on the grip 136 for indicating an angular position of the grip 136.

In various embodiments, the pawl mount 404 is secured to the handle and/or the take-up chamber 132 using adhesives, welds, fasteners, and/or the like. A pawl lock 108 illustrated in FIG. 5 (and FIGS. 1 and 3) is an example of a fastener used for securing the pawl mount 404 to the handle 102. The pawl lock 108 includes snap projections 518 for engaging an inner surface of the pawl mount 404 and securing the pawl 402. Four snap projections 518 are illustrated in FIG. 5, however, 1, 2, 3, 5, 6, 7, 8, 9, 10, or more snap projections 518 may be used. Various components are illustrated as being fabricated as a single piece, including the source spool 501; the lid 124; the bobbin 134; the pawl lock 108; the pawl mount 404 and pawl 402; the projection 112, button assembly 104, and the body 500.

FIG. 10 is a side elevation of internal parts of the flosser 100 of FIG. 1. The various components of FIG. 9 (e.g., the handle, the source chamber 122, take-up chamber 132, the head 110 the bobbin 134, the bobbin lock 306, the pawl 402 and pawl mount 404, the pawl lock 108, the button assembly 104, the lid 124, the spool 501, and the projection 112) are shown in their relative assembled positions. In some embodiments, the handle, the source chamber 122, take-up chamber 132, and the head 110 are fabricated from a single piece of material, for example using injection molding processes.

In FIG. 10. the handle, the source chamber 122, the take-up chamber 132, and the head 110 are omitted for clarity. For illustration purposes, the remaining components in FIG. 10, including the bobbin 134, the bobbin lock 306, the pawl 402 and pawl mount 404, the pawl lock 108, the button assembly 104, the lid 124, the spool 501, and the projection 112 are shown in their assembled positions relative to the omitted parts (handle, source chamber 122, take-up chamber 132, and head 110) and to each other. The floss 106 is also shown and labeled in subsections for illustrating an exemplary path.

FIG. 9 differs from FIG. 10 in that the body 500 is omitted from FIG. 10 and the internal parts are shown in elevation instead of cross section. FIG. 9 further differs from FIG. 10 in that FIG. 9 illustrates the button assembly 104 in the engagement position, discussed elsewhere herein. FIG. 10 illustrates the button assembly 104 in the disengagement position, discussed elsewhere herein. The Button assembly 104 is configured to rotate about the pivot 522 to move the engagement pawl 524 (double arrow) between a position of engagement with the cog 502 (FIG. 9) and disengagement with the cog 502 (FIG. 10). The spring 526 may bias the button assembly 104 in a position for engaging the cog 502.

FIG. 10 further illustrates a path for routing floss 106 from the source spool 501 along the head 110 into suspension between the projection 112 and the feed guide, 114, through the feed guide 114, around the source assembly 120, along the handle 102 and to the take-up bobbin 134. The path is illustrated in FIG. 10 as path segments 106a-106m.

Before use, floss 106 is wrapped around the spindle 504 of the source spool 501 at path segment 106a. Along path segment 106b, floss may pass through the first aperture 540 and along channel 542 to the second aperture 544. At path segment 106c, floss 106 may pass through the second aperture from the upper to the lower of the head 110. At path segment 106d, floss is suspended between the second aperture 544 and the projection aperture 116. At path segment 106e, floss may be suspended between the projection aperture 116 and the feed guide 114.

During use, floss 106 that is suspended between the projection aperture 116 and the feed guide 114, the projection 112 may be inserted between a brace wire or arch wire and interproximal space or contacts between a pair of adjacent teeth. Insertion of the projection 112 inserts the projection aperture 116, thus, the floss 106 below the brace wire. Thus, the floss 106 may be used for cleaning the interproximal spaces between the teeth including below the brace wire.

After use, floss 106 may traverse from the lower to the upper side of the head 110 along path segment 106f through the feed guide 114. Along path segment 106g, floss 106 may move along channel 546 from the upper end of the feed guide 114 to the third aperture 548. At path segment 106h, floss 106 may traverse from the upper side of the head 110 to the groove 408 around the source chamber 122. Groove 408 may allow gripping the source chamber 122 and manipulation of the flosser 100 without touching floss 106 as it travels around the source chamber along path segment 106i from the third aperture 548 to the fourth aperture 550. At path segment 106j, floss 106 may traverse through the fourth aperture 550 from the lower to upper side of the handle 102. Along path segment 106k, floss 106 may travel along the handle channel 552 from the source assembly 120 to the take-up assembly 130. The handle channel 552 may allow gripping the handle 102 and manipulating the flosser 100 without touching floss 106 that may have contamination and debris as the floss 106 travels the length of the handle 102 along path segment 106k from the fourth aperture 550 to the fifth aperture 554. At the path segment 106m, floss 106 passes through aperture 554 into the take-up chamber 132. After use, floss 106 may be wrapped around the spindle 906 of the take-up bobbin 134 at path segment 106a. The path including path segments 106a-106m is an example of a routing of floss 106 from a source spool to a take-up bobbin. Alternative routing of floss 106 may be used in various embodiments of the flosser 100.

Figure 11:
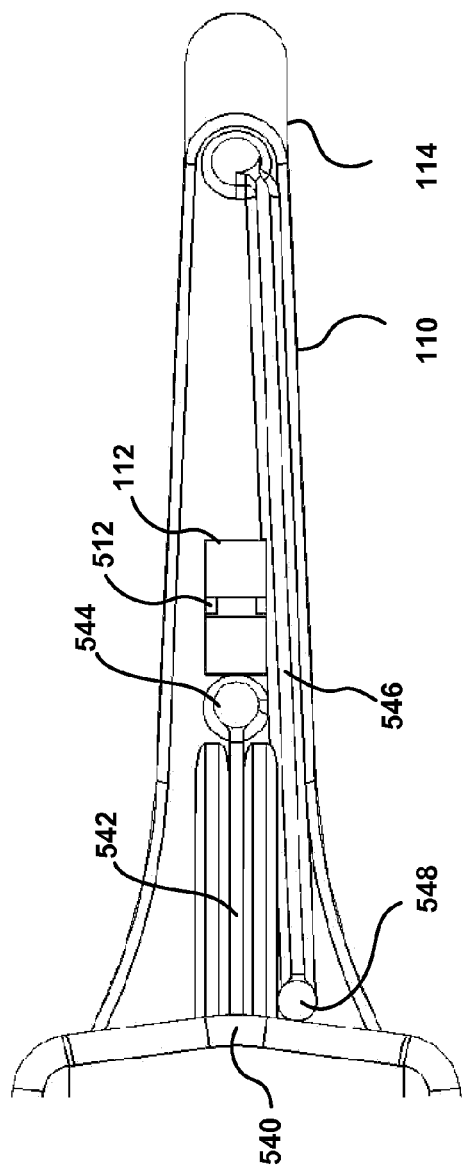
FIG. 11 is an enlargement of a portion of FIG. 3 showing details of the head of the flosser.

FIG. 11 is an enlargement of a portion of FIG. 3 showing details of the head 110 of the flosser 100. FIG. 11 illustrates details of the first aperture 540, the channel 542 the second aperture 544, the upper end of the feed guide 114, channel 546, and the third aperture 548. Additional details of the projection 112 are also illustrated.

Figure 12:
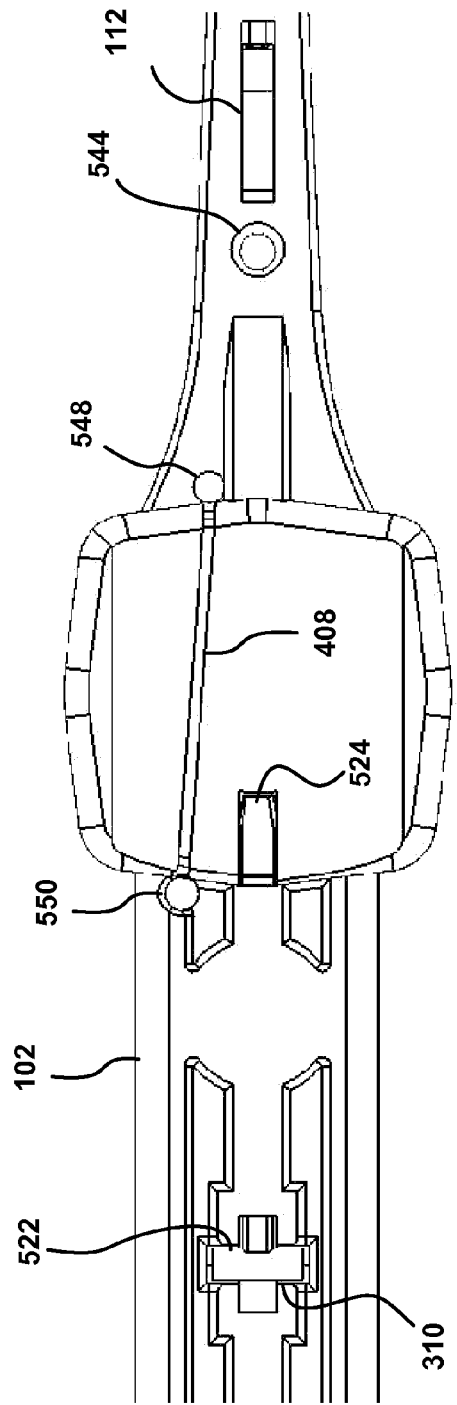
FIG. 12 is an enlargement of a portion of FIG. 4 showing details of the source chamber and portions of the head and handle.

FIG. 12 is an enlargement of a portion of FIG. 4 showing details of the source chamber 122 and portions of the head 110 and handle 102. FIG. 12 illustrates details of the second aperture 544, the third aperture 548, the fourth aperture 550, and groove 408. Additional details of the engagement pawl 524, the button socket 310 and the pivot 522 are also illustrated.

Figure 13:
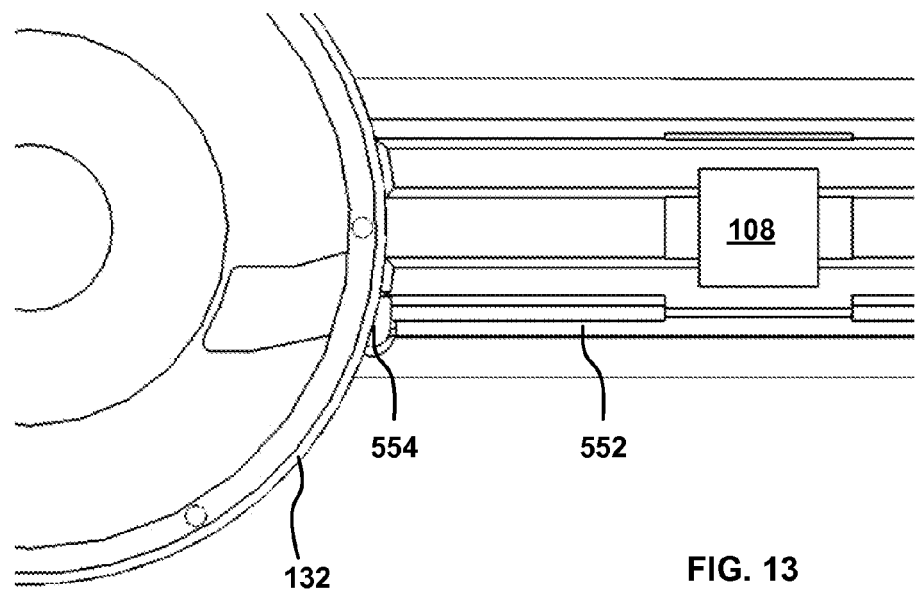
FIG. 13 is an enlargement of a portion of FIG. 3 showing details of the take-up spool and handle of the flosser of FIG. 1.

FIG. 13 is an enlargement of a portion of FIG. 3 showing details of the take-up bobbin 134 and handle 102 of the flosser 100 of FIG. 1. FIG. 13 illustrates details of a portion of the handle channel 552 and the fifth aperture 554.

Figure 14:
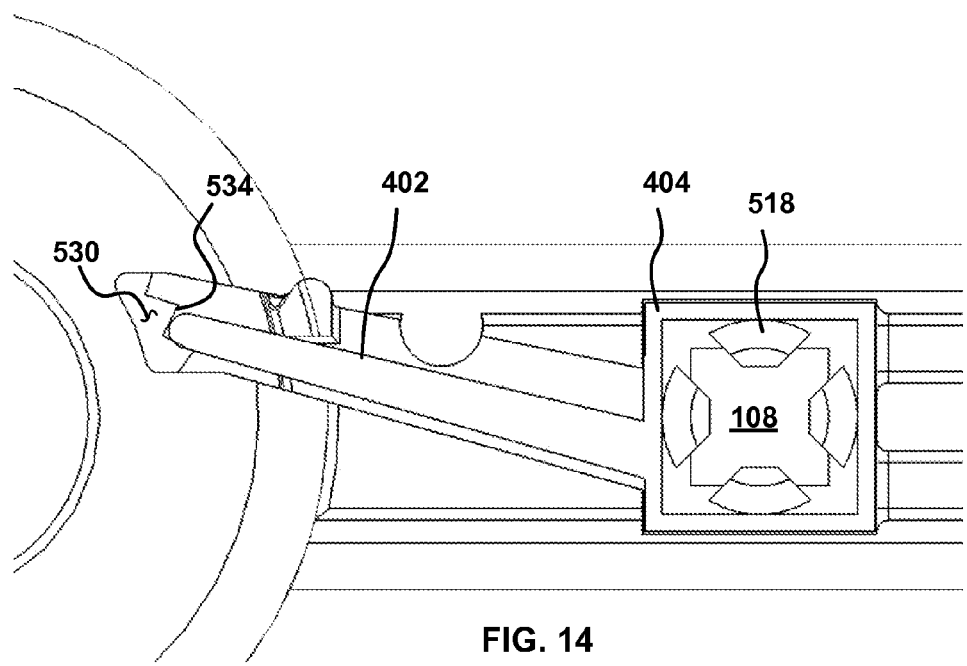
FIG. 14 is an enlargement of a portion of FIG. 4 showing details of the take-up chamber, pawl, and handle of the flosser of FIG. 1.

FIG. 14 is an enlargement of a portion of FIG. 4 showing details of the take-up chamber 132, pawl 402, and handle 102 of the flosser 100 of FIG. 1. Details of an engagement between the ratchet 530 and the pawl are illustrated. In some embodiments, the pawl is about normal to a face 534 of the ratchet. The face 534 may also be about normal to an adjacent face. For purposes of the face 534 of the ratchet, about normal is an angle less than about 12 degrees. An engagement at about a right angle minimizes backlash of the ratchet. When the face 534 of the ratchet tooth is essentially tangent to an arc described by the end of the pawl, the ratchet 530 has minimal retrograde movement as the pawl moves from the point of the ratchet tooth to the face 534. Moreover, force applied by the face 534 to the pawl is in the axis of the pawl, thus, there is minimal or no side load on the pawl. This reduces stress where the pawl 402 joins the pawl mount 404. FIG. 14 further illustrates details of engagement of the snap projections 518 in the pawl mount 404.

Figure 15:
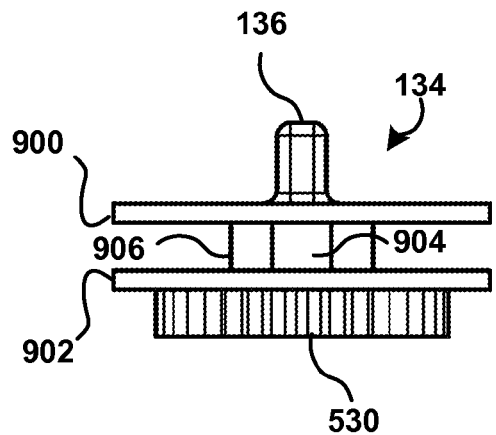
FIG. 15 is a side elevation of the take-up bobbin of FIG. 15, in accordance with aspects of the technology.
Figure 16:
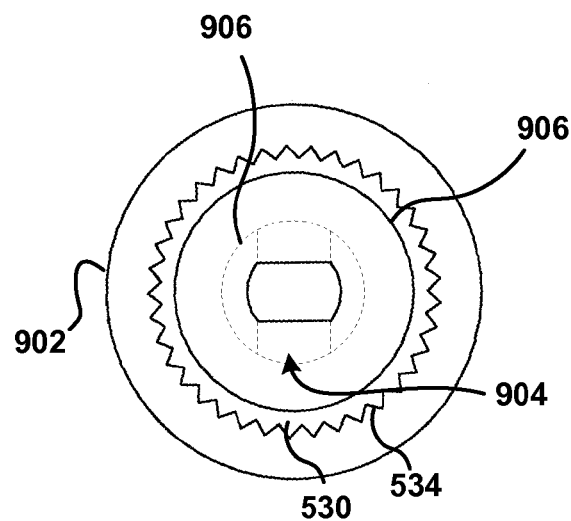
FIG. 16 is a bottom plan view of a take-up bobbin of FIG. 1, in accordance with aspects of the technology.

FIG. 15 is a side elevation of the take-up bobbin 134 of FIG. 1, in accordance with aspects of the technology. FIG. 16 is a bottom plan view of a take-up bobbin 134 of FIG. 15, in accordance with aspects of the technology. The take-up bobbin 134 of FIGS. 15 and 16 includes the spindle 906 and the spindle aperture 904. The spindle 906 and an outline of the spindle aperture 904 are shown in dotted line in FIG. 16 to indicate that they are not visible from the bottom plan view. Floss 106 may be threaded through the spindle aperture 904 and secured to the spindle 906, e.g., using a knot. Upon rotating the take-up bobbin 134, floss may wrap around the spindle 906. The take-up bobbin 134 may further include an upper flange 900 and a lower flange 902. The upper flange 900 is configured to contain debris and contamination within the take-up chamber 132. The lower flange 902 is configured to support the ratchet 530 and prevent floss 106 from tangling about the ratchet 530 and the pawl 402.

In some embodiments, antimicrobial agents are infused into the floss 106 for inhibiting transfer of bacteria between surfaces of teeth, braces, and from one contact to another. For example, floss 106 may be permeated with chlorhexidine gluconate to inhibit survival of bacterial and other microbes in the floss 106 during use and to inhibit deposition of microbes on the surfaces of teeth, contacts, and/or braces. Various antimicrobial agents include chlorhexidine gluconate, Triclosan, hydrogen peroxide, carbamide peroxide, and cetylpyridinium chloride. Environmentally friendly antimicrobial agents may be used, including an extract of magnolia bark, xylitol (a sugar alcohol that is naturally occurring in Birch and fruits), and antimicrobial peptides, which are compounds that are found throughout the animal and plant kingdom such as HNP (human neutrophil proteins). The floss 106 may also be infused with anti-cavity agents such as fluorides, e.g., sodium fluoride, hexafluorosilicic acid (H2SiF6) and its salt sodium hexafluorosilicate (Na2SiF6), and/or the like. The floss 106 may also be used for depositing the antimicrobial and/or anti-cavity agents on the surfaces of teeth and/or braces. In some embodiments, the antimicrobial agent may be applied to the floss 106 as the floss 106 is dispensed from the source spool 501 during use. For example, the floss 106 may be routed through a reservoir of antimicrobial agent (not illustrated) disposed on the handle 102, the head 110, on the source chamber 122, and/or within the source chamber 122. The reservoir may be configured to apply the antimicrobial agent to the floss 106 during transit. The above antimicrobial and anti-cavity agents may be used individually or in various combinations and mixtures.

Figure 17:
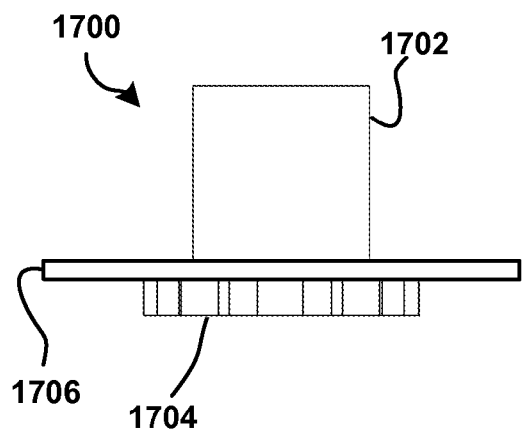
FIG. 17 is a side elevation of an alternative embodiment of the source spool of FIG. 5, in accordance with aspects of the technology.

FIG. 17 is a side elevation of an alternative embodiment of the source spool of FIG. 5, in accordance with aspects of the technology. The source spool 1700 differs from the source spool 501 of FIG. 5 in that the source spool 1700 includes a flange 1706. The source spool 1700 includes a spindle 1702 and a cog 1704, similar to the spindle 504 and the cog 502, respectively, of the source spool 501. The flange 1706 is configured to prevent tangling of floss 106 during winding onto the source spool 1700. Some types of automated winding equipment fail to sense a transition between the spindle the cog 1704 resulting in an attempt to wind floss 106 too close to, or even onto, the cog 1704 with undesirable results. The flange 1706 reduces winding of floss 106 on the spindle 1702 too close or onto the cog 1704.

In some embodiments, the floss 106 is impregnated with an anti-microbial agent. Examples of anti-microbial agents include 5-chloro-2-(2,4-dichlorophenoxy)phenol (Triclosan), chlorhexidine gluconate, hydrogen peroxide, carbamide peroxide, and cetylpyridinium chloride. Environmentally friendly antimicrobial agents may be used, including an extract of magnolia bark, xylitol (a sugar alcohol that is naturally occurring in Birch and fruits), and antimicrobial peptides, which are compounds that are found throughout the animal and plant kingdom such as HNP (human neutrophil proteins). The floss 106 may also be infused with anti-cavity agents such as fluorides, e.g., sodium fluoride, hexafluorosilicic acid ($H_2SiF_6$) and its salt sodium hexafluorosilicate ($Na_2SiF_6$), and/or the like. The floss 106 may also be used for depositing the antimicrobial and/or anti-cavity agents on the surfaces of teeth and/or braces. In some embodiments, the antimicrobial agent may be applied to the floss 106 as the floss 106 is dispensed from the source spool 501 during use. For example, the floss 106 may be routed before use through a reservoir (not illustrated) of antimicrobial agent disposed on the handle 102, in the source chamber 122, or external to the source chamber 122. The reservoir may be configured to apply the antimicrobial agent to the floss 106 during transit. The above antimicrobial and anti-cavity agents may be used individually or in various combinations and mixtures.

Figure 18:
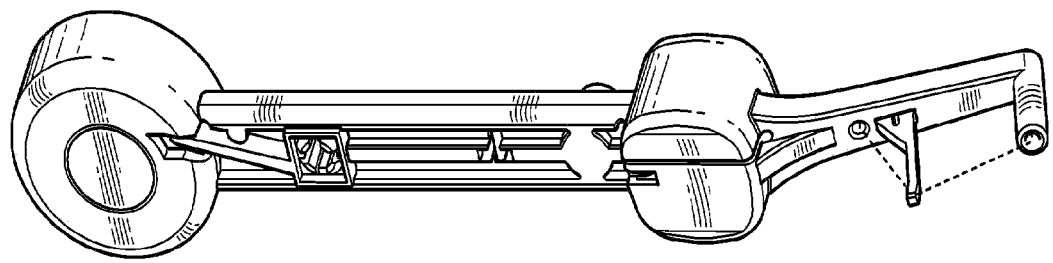
FIG. 18 is a bottom perspective view of the flosser of FIG. 1.
Figure 19:
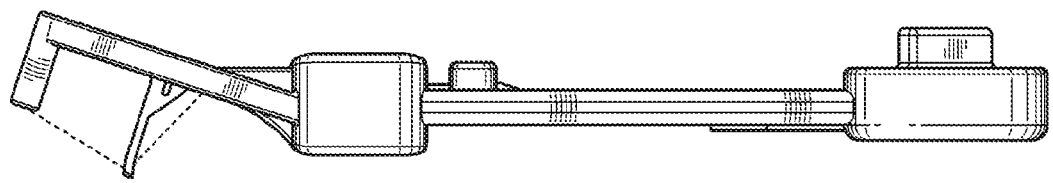
FIG. 19 is a left side elevation of the flosser of FIG. 1.

FIG. 18 is a bottom perspective view of the flosser 100 of FIG. 1. FIG. 19 is a left side elevation of the flosser 100 of FIG. 1. FIGS. 18-19 are provided to provide additional views of the flosser 100.

Figure 20:
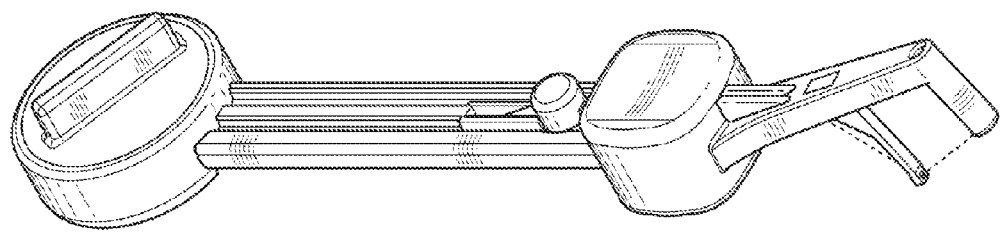
FIG. 20 is a top perspective view of an alternative embodiment of a flosser, in accordance with aspects of the technology.
Figure 21:
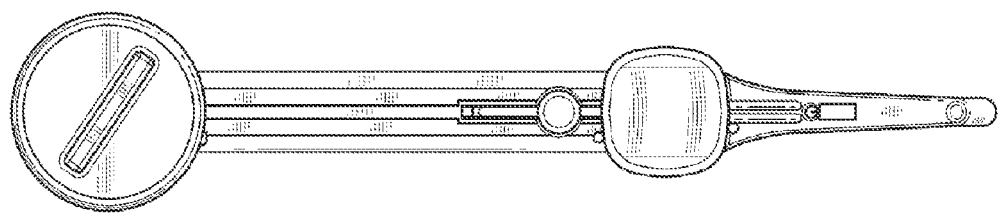
FIG. 21 is a top plan view of the flosser of FIG. 20.
Figure 22:
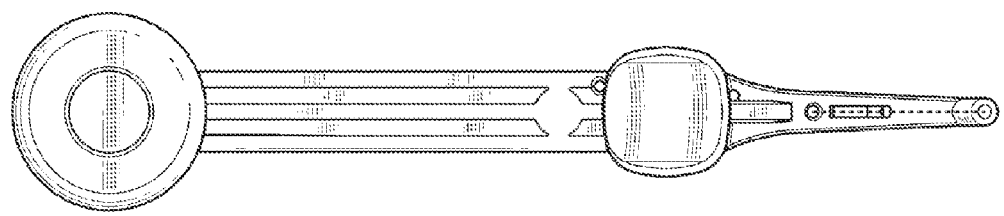
FIG. 22 is a bottom plan view of the flosser of FIG. 20.
Figure 23:
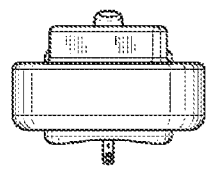
FIG. 23 is a rear elevation view of the flosser of FIG. 20.
Figure 24:
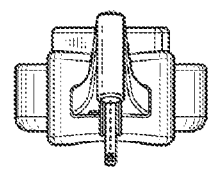
FIG. 24 is a front elevation view of the flosser of FIG. 20.
Figure 25:
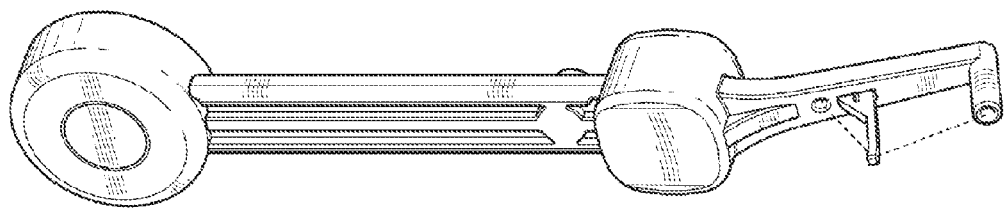
FIG. 25 is a bottom perspective view of the flosser of FIG. 20.
Figure 26:
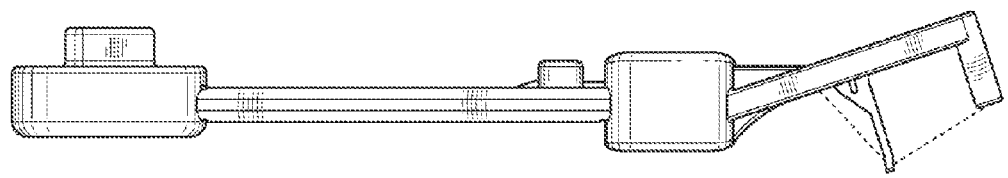
FIG. 26 is a right side elevation of the flosser of FIG. 20.
Figure 27:
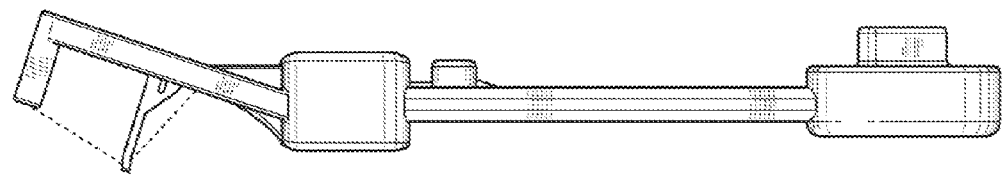
FIG. 27 is a left side elevation of the flosser of FIG. 20.

FIG. 20 is a top perspective view of an alternative embodiment of a flosser, in accordance with aspects of the technology. FIG. 21 is a top plan view of the flosser of FIG. 20. FIG. 22 is a bottom plan view of the flosser of FIG. 20. FIG. 23 is a rear elevation view of the flosser of FIG. 20. FIG. 24 is a front elevation view of the flosser of FIG. 20. FIG. 25 is a bottom perspective view of the flosser of FIG. 20. FIG. 26 is a right side elevation of the flosser of FIG. 20. FIG. 27 is a left side elevation of the flosser of FIG. 20.

The embodiments discussed herein are illustrative. As these embodiments are described with reference to illustrations, various modifications or adaptations of the methods and/or specific structures described may become apparent to persons of ordinary skill in the art. Various features and aspects of the above described technology may be used individually or jointly. Features in each of the various illustrations may be combined with features in other illustrations or used individually for illustrating the present technology. All such modifications, adaptations, or variations that rely upon the teachings of the embodiments, and through which these teachings have advanced the art, are considered to be within the spirit and scope of the present application. Hence, these descriptions and drawings should not be considered in a limiting sense, as it is understood that the present application is in no way limited to only the embodiments illustrated.

What is claimed is:

1. A flosser for cleaning a contact between two teeth proximate a wire brace, the flosser comprising:
   a handle, extending along a longitudinal axis from a first end to a free second end;
   a head coupled to the handle, the head and the handle forming an obtuse upward angle, relative to the longitudinal axis of the handle;
   a source spool coupled to the first end of the handle for dispensing floss to the head;
   a button configured to move an engagement pawl to a disengagement position to permit rotation of the source spool when pressed for dispensing the floss, the engagement pawl configured to prevent rotation of the source spool when the button is not pressed for applying tension to the floss;
   a first floss support coupled to the head and extending downward from the head and relative to the longitudinal axis
   a second floss support extending downward from the head, the second floss support about parallel to the first floss support and including an aperture sized for feeding the floss from the source spool into suspension between the first and second floss support, the second floss support shaped for insertion of the aperture into a space between the wire brace and the two teeth for cleaning the contact between the two teeth using suspended floss;
   a take-up bobbin coupled to the free second end of the handle for receiving floss from the head, the take-up bobbin and the source spool both external to the handle; and a pawl lock located on the handle adjacent the take-up bobbin, the pawl lock configured to engage a pawl engaging the take-up bobbin, the button and the pawl lock being positioned between the source spool and the take-up bobbin.

2. The flosser of claim 1, wherein the angle between the head and the longitudinal axis of the handle is between about 10 degrees and about 20 degrees.

3. The flosser of claim 1, wherein the second support is longer than the first support.

4. The flosser of claim 1, wherein the second support is closer to the handle than the first support.

5. The flosser of claim 1, further comprising a ratchet coupled to the take-up bobbin, an end of the elongated pawl configured to engage an opposing face of a ratchet tooth of the ratchet, a longitudinal axis of the elongated pawl about normal to the opposing face of the ratchet tooth.

6. The flosser of claim 1, further comprising a grip configured for rotating the take-up bobbin.

7. The flosser of claim 1, wherein the take-up bobbin includes a grip and a ratchet, the take-up bobbin, the grip, and the ratchet fabricated as one single entire unitary piece.

8. The flosser of claim 1, further comprising an anti-microbial agent disposed in the suspended floss including chlorhexidine gluconate.

9. A flosser comprising:
   a floss support having an aperture configured for slidably supporting floss, the floss support sized for insertion of the aperture between a wire mounted on a pair of adjacent teeth and an interproximal space between the teeth;
   a floss guide about parallel to the floss support and configured for slidably supporting floss in suspension between the aperture and the floss guide;
   a head for supporting the floss support and the floss guide;
   a source spool configured for rotatably dispensing floss to the floss support;
   a button assembly adjacent the source spool configured to release the source spool for rotation when a button of the button assembly is pressed and to prevent rotation of the source spool when the button is not pressed;
   a source chamber configured to enclose the source spool to prevent contamination of floss on the source spool, the source chamber further configured to support the head;
   a receiving spool configured for rotatably receiving floss after use, the receiving spool including a ratchet configured for unidirectional rotation of the receiving spool and to hold tension on the floss when the button is not pressed;
   an elongated pawl configured to engage an opposing face of a ratchet tooth, a long axis of the elongated pawl about normal to the opposing face;
   a receiving chamber configured to enclose the receiving spool to contain contamination on the received floss; and
   a handle extending along a longitudinal axis from a first end to a free second end, the handle coupled to the head and configured to separate the source chamber at the first end of the handle and the receiving chamber at the free second end of the handle, both the source and receiving chamber being external to the handle, the longitudinal axis of the handle forming an obtuse angle with respect the head; and a pawl lock located on the handle adjacent the receiving chamber, the pawl lock configured to engage the elongated pawl, the button assembly and the pawl lock being position between the source spool and the receiving spool.

10. The flosser of claim 9, wherein the floss support is longer than the floss guide.

11. The flosser of claim 9, wherein the engaged opposing face of the ratchet tooth is about normal to an adjacent face of an adjacent ratchet tooth.

12. The flosser of claim 9, wherein the handle includes a channel in an external surface of the handle, the channel configured to conduct the floss between the floss guide and the receiving spool without interfering with gripping the external surface of the handle.

13. The flosser of claim 12, wherein an external surface of the source chamber includes a groove configured to conduct floss between the head and the handle without interfering with gripping the source chamber.

14. The flosser of claim 9, wherein the angle between the longitudinal axis of the handle and the head is between ten degrees and twenty degrees.

15. An apparatus for cleaning teeth comprising:
   an elongated handle extending along a longitudinal axis from a first end to a free second end;
   a source chamber and receiving chamber coupled to the first end and the free second end of the elongated handle respectively, both the source chamber and receiving chamber being external to the handle;
   a head coupled to the source chamber distal the first end of the elongated handle and configured to form an upward angle between the head and the longitudinal axis of the elongated handle;
   a pair of projections depending downward from the head in a plane of the upward angle and configured to slidably suspend fresh floss under tension;

a first spool including cogs and disposed in the source chamber, the first spool configured to provide fresh floss to the pair of projections and use the cog to maintain resistance to tension on the fresh floss during use of the fresh floss for cleaning teeth;

a second spool disposed in the receiving chamber and configured to apply tension to the fresh floss when resistance to tension is maintained at the first spool and to receive used floss from the pair of projections when resistance to tension is released at the first spool;

a button assembly located adjacent to the first spool, the button assembly configured to move a pawl connected to the button assembly from between the cogs to release resistance to tension at the first spool; and a pawl lock configured to secure an elongated pawl to the elongated handle adjacent the free second end, the elongated pawl configured to engage the second spool, the button assembly, the elongated pawl and the pawl lock disposed between the first spool and the second spool.

16. The apparatus of claim 15, further comprising a ratchet disposed on the second spool and configured to engage the elongated pawl to apply unidirectional rotation to the second spool.

17. The apparatus of claim 15, further comprising a longitudinal channel along an exterior surface of the handle for providing free movement of used floss along the handle while gripping the exterior surface of the handle.

18. The apparatus of claim 15, further comprising an antimicrobial agent impregnating the fresh floss.

19. The apparatus of claim 15, wherein the upward angle is between about twelve degrees and about seventeen degrees.

20. The apparatus of claim 15, wherein the first chamber is configured to couple the handle to the head and the elongated handle is configured to separate the first chamber from the second chamber.

* * * * *